(12) United States Patent
Youngblood et al.

(10) Patent No.: US 8,246,244 B2
(45) Date of Patent: Aug. 21, 2012

(54) CONTAINERS USED IN DETERMINING THE THERMAL STABILITY OF FUELS

(75) Inventors: Larry M. Youngblood, Houston, TX (US); David G. Anderson, San Antonio, TX (US); Guoxing Yang, Pearland, TX (US); Scott K. Berkhous, Spring, TX (US); Larry A. Spino, Houston, TX (US)

(73) Assignee: Petroleum Analyzer Company LP, Houston, TX (US)

( * ) Notice: Subject to any disclaimer, the term of this patent is extended or adjusted under 35 U.S.C. 154(b) by 236 days.

(21) Appl. No.: 12/861,595

(22) Filed: Aug. 23, 2010

(65) Prior Publication Data

US 2012/0014406 A1 Jan. 19, 2012

Related U.S. Application Data

(63) Continuation-in-part of application No. 12/838,104, filed on Jul. 16, 2010.

(51) Int. Cl.
 G01N 33/22 (2006.01)
 G01N 25/00 (2006.01)
 G01N 1/10 (2006.01)
(52) U.S. Cl. ........................ 374/43; 73/61.62; 73/864.91
(58) Field of Classification Search .................... 374/43, 374/45, 57, 137; 73/61.62, 61.71, 61.72, 73/61.76, 864.81, 864.83, 864.84, 864.85, 73/864.91
See application file for complete search history.

(56) References Cited

U.S. PATENT DOCUMENTS

| 3,417,605 | A | * | 12/1968 | Hahn | 73/23.2 |
|---|---|---|---|---|---|
| 3,670,561 | A | | 6/1972 | Hundere | |
| 3,879,264 | A | * | 4/1975 | Seelbach | 196/46.1 |
| 4,576,197 | A | | 3/1986 | Kempers | |
| 5,101,658 | A | | 4/1992 | Wilson, III et al. | |
| 5,337,599 | A | | 8/1994 | Hundere et al. | |
| 5,401,661 | A | | 3/1995 | Florkowski et al. | |
| 5,498,400 | A | * | 3/1996 | Hill | 423/300 |
| 5,662,417 | A | | 9/1997 | Tyus | |
| 5,783,720 | A | * | 7/1998 | Mendicino et al. | 556/470 |
| 5,908,995 | A | | 6/1999 | Pauchon et al. | |

(Continued)

FOREIGN PATENT DOCUMENTS

KR 2005116180 A * 12/2005

(Continued)

OTHER PUBLICATIONS

JFTOT 230 Mark III Jet Fuel Thermal Oxidation Tester User's Manual, Alcor, PN: AL-59322, Rev. E , Aug. 14, 2008.

(Continued)

*Primary Examiner* — R. A. Smith
(74) *Attorney, Agent, or Firm* — Gunn, Lee & Cave, P.C.

(57) ABSTRACT

A thermal oxidation tester is shown for determining thermal stability of a fluid, particularly hydrocarbons, when subjected to elevated temperatures. The tendency of the heated fluid to oxidize and (1) form deposits on a surface of a heater tube and (2) form solids therein which are both measured at a given flow rate, temperature and time. The measured results are used to determine whether a fluid sample passes or fails the test. Specifically constructed containers used in a thermal oxidation tester are shown. These containers (1) reduce physical contact to hydrocarbon test fuels, (2) reduce exposure to hydrocarbon fuel vapors, (3) reduce environmental impact by reducing chemical spills, and (4) improve overall work flow of test.

27 Claims, 9 Drawing Sheets

U.S. PATENT DOCUMENTS

| | | | |
|---|---|---|---|
| 6,099,724 A | 8/2000 | Dourdeville | |
| 6,119,534 A * | 9/2000 | Dinsmore | 73/864.91 |
| 6,370,946 B1 | 4/2002 | Lacey et al. | |
| 6,558,361 B1 | 5/2003 | Yeshurun | |
| 7,093,481 B2 | 8/2006 | Morris | |
| 2003/0150153 A1 | 8/2003 | Henry, Jr. et al. | |
| 2010/0269599 A1 * | 10/2010 | Schroeter et al. | 73/863.12 |

FOREIGN PATENT DOCUMENTS

| | | | |
|---|---|---|---|
| SU | 1249456 A * | 8/1986 | |

OTHER PUBLICATIONS

Maxim, DS2433X Flip Chip Pkg, 1.10 MM Pitch Pkg Code BF623-3, Walker, Jeff, Jul. 16, 2008, Rev. A, effective date Jul. 16, 2008.
JFTOT® 230 Mark III, "Smaller, Simpler, Faster. Improved Controls for Jet Fuel Stability Analysis." PAC, 2 pages.
JFTOT, "Video Tube Deposit Rater", PAC, 2 pages.
ASTM D 3241-09, "Standard Test Method for Thermal Oxidation Stability of Aviation Turbine Fuels (JFTOT Procedure)", ASTM International, 14 pages.
"Seal-All®—Gas & Oil-Resistant Adhesive" web page.

* cited by examiner

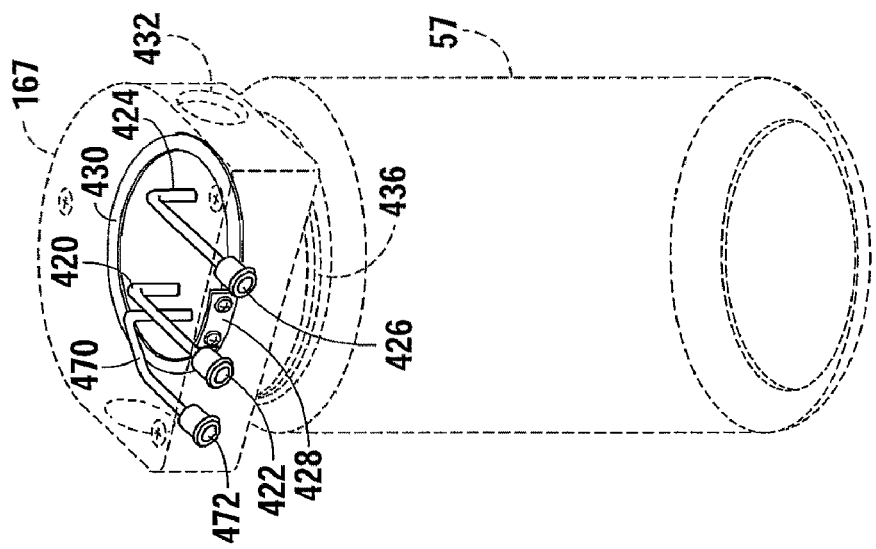
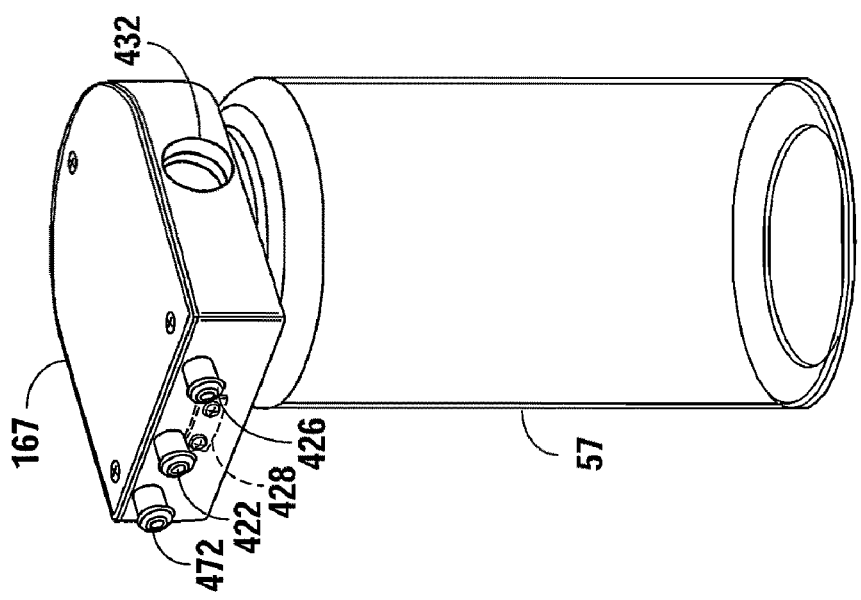

CONTAINERS USED IN DETERMINING THE THERMAL STABILITY OF FUELS

CROSS REFERENCE TO RELATED APPLICATIONS

This is a continuation-in-part of U.S. patent application Ser. No. 12/838,104, filed on Jul. 16, 2010, having at least one overlapping inventor and the same assignee.

BACKGROUND OF THE INVENTION

1. Technical Field

This invention relates to methods and devices for measuring the thermal characteristics of fuels. Specifically, this invention relates to containers used in measuring the thermal oxidation tendencies of fuels for liquid hydrocarbon-burning engines.

2. Background Art

When engines were developed for use in jet aircraft, problems began to develop for jet fuel due to poor fuel thermal stability. At higher temperatures, the jet fuels would oxidize and form deposits that would clog fuel nozzles and fuel filters. These deposits would also collect in the jet engine.

While various tests were devised and used in the 1950s and 60s to rate the thermal oxidation characteristics of jet fuels prior to being used in jet aircraft, Alf Hundere developed the apparatus and method which became the standard in the industry. In 1970, Alf Hundere filed what became U.S. Pat. No. 3,670,561, titled "Apparatus for Determining the Thermal Stability of Fluids". This patent was adopted in 1973 as ASTM D3241 Standard, entitled "Standard Test Method for Thermal Oxidation Stability of Aviation Turbine Fuels", also known as the "JFTOT® Procedure". This early Hundere patent was designed to test the deposition characteristics of jet fuels by determining (1) deposits on the surface of a heater tube at an elevated temperature and (2) differential pressure across a filter due to collection of particulate matter. To this day, according to ASTM D3241, the two critical measurements are still (1) the deposits collected on a heater tube and (2) differential pressure across the filter due to the collection of particulate matter on the filter.

According to ASTM D3241, 450 mL of fuel flows across an aluminum heater tube at a specified rate, during a 2.5 hour test period at an elevated temperature. Currently six different models of JFTOT®[1] instruments are approved for use in the ASTM D3241-09 Standard. The "09" refers to the current revision of the ASTM D3241 Standard.

[1] JFTOT is the registered trademark of Petroleum Analyzer Company, LP.

While over the years various improvements have been made in the apparatus to run the tests, the basic test remains the same. Improvements in the apparatus can be seen in U.S. Pat. Nos. 5,337,599 and 5,101,658. The current model being sold is the JFTOT 230 Mark III, which is described in further detail in the "Jet Fuel Thermal Oxidation Tester—User's Manual". The determination of the deposits that occur on the heater tube can be made visually by comparing to known color standards or can be made using a "Video Tube Deposit Rater" sold under the Alcor mark.

The determination of the amount of deposits formed on the heater tube at an elevated temperature is an important part of the test. The current ASTM D3241 test method requires a visual comparison between the heater tube deposits and known color standard. However, this involves a subjective evaluation with the human eye. To take away the subjectivity of a person, an electronic video tube deposit rater was developed.

Also, there has been considerable discussion as to the polish or finish of the heater tube. (See U.S. Pat. No. 7,093,481 and U.S. Patent Application Publication No. US 2002/083,760.) The finish of the heater tube is very important in determining the amount of fuel deposits that will form thereon. Therefore, it is important that the quality of the finish on heater tubes made today be consistent with the finish of heater tubes made since 1973.

In the past, containers used for (1) the test sample or (2) waste fuel had limitations. The containers were primarily open vessels that did not provide the operator feedback about being securely positioned, did not contain or capture fuel vapors, and were difficult to secure in place. Aeration of the test sample while in the container also requires a coarse glass dispersion tube.

BRIEF SUMMARY OF THE INVENTION

It is an object of the present invention to provide an apparatus and method for testing thermal oxidation stability of fluids, particularly aviation fuels.

It is another object of the present invention to provide special purpose containers for an apparatus and method to measure the tendency of fuels to form deposits when in contact with heated surfaces.

It is another objective of the present invention to provide containers with aeration and venting for an apparatus and/or method for testing the thermal oxidation tendency of fuels utilizing a test sample to determine if solid particles will form in the fuel at an elevated temperature and pressure.

It is another objective of the present invention to provide a sample container to retain and aerate the fuel being tested and a waste container to receive spent fuel after the test as part of an apparatus and method for determining thermal oxidation stability of fuel by testing a sample at an elevated temperature and pressure to determine (1) deposits that form on a metal surface and (2) solid particles that form in the fuel.

It is another objective of the present invention to provide an apparatus and method for holding a test sample, aerating the test sample, delivering the test sample as needed for testing and collecting the spent test sample after the test.

It is yet another objective of the present invention to provide an aeration device to keep a test sample saturated with dry air during a thermal oxidation stability test.

It is another objective of the present invention to have an apparatus and method to deliver a test fuel saturated with dry air to a thermal oxidation stability test and collect spent fuel after the test, containers for the test fuel and spent fuel being easily connected and monitored to make sure the containers are properly connected.

A sample container arm is provided that (1) threadably connects to the sample container and (2) plugs into the apparatus for testing thermal oxidation stability of fuels. The sample container arm performs the following functions:
  (a) connects an aeration frit located in the bottom of the sample container to an aeration pump;
  (b) provides a connection to the embedded computer to measure the temperature of the test sample contained in the sample container;
  (c) provides a connection so that the sample drive pump can draw a test sample from the sample container when performing the test;
  (d) provides a vent connection to atmosphere to maintain the sample container at a atmospheric pressure; and
  (e) uses the temperature sensor connected to the imbedded computer to determine if the sample container arm along with the sample container are in position.

The sample container arm also has a seal to secure it to the top of the sample container with the sample container arm.

A waste container arm also connects to the apparatus performing the thermal oxidation stability test. The waste container arm resembles the sample container arm. The waste container arm also has a seal to secure it to the top of the waste container with the waste container arm. The waste container arm performs the following functions:

(a) Receives spent or waste fuel after the test has been performed thereon;
(b) Receives vented and/or flushed fuel or air from the test apparatus during start-up or shut-down;
(c) Provides a vent to atmosphere to maintain the waste container at atmospheric conditions; and
(d) Provides an electrical feedback to the embedded computer indicating the waste container arm and the waste container are in position.

To ensure the test sample is fully aerated prior to the test, a glass frit is connected on the lower end of the aeration line inside of the sample container. The aeration frit is made out of coarse glass bonded to a cap that attaches to the aeration fitting. This configuration allows unimpeded airflow into the test liquid.

BRIEF DESCRIPTION OF THE DRAWINGS

FIG. 7A is a perspective view of the waste container.

FIG. 7B is a perspective view of the internal components of the waste container.

DESCRIPTION OF THE PREFERRED EMBODIMENT

Figure 1:
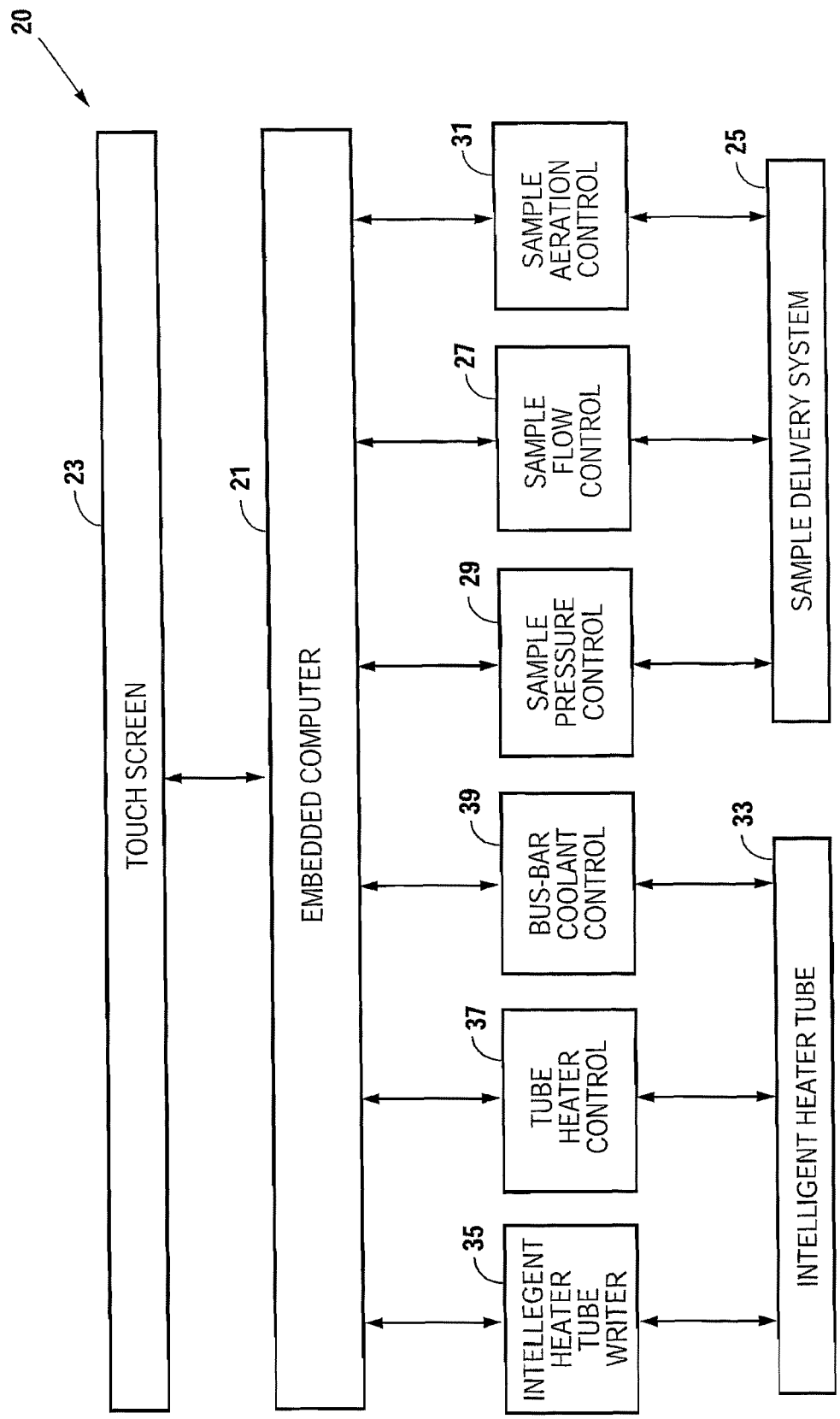
FIG. 1 is a general block diagram of a thermal oxidation stability test apparatus illustrating flow and electrical controls.

FIG. 1 is a schematic block diagram of a thermal oxidation stability tester referred to generally by the reference numeral 20. The thermal oxidation stability tester 20 has an embedded computer 21 with a touch screen 23 for user interface. While many different types of programs could be run, in the preferred embodiment, applicant is running C++ in the embedded computer 21. The touch screen 23 displays all of the information from the thermal oxidation stability tester 20 that needs to be conveyed to the user. The user communicates back and forth with the embedded computer 21 through the touch screen 23. If a batch of fuel is to be tested, a test sample is put in the sample delivery system 25.

It is important to the test to make sure the test sample is oxygen saturated through aeration. Therefore, the embedded computer 21 operates a sample aeration control 31 for a period of time to make sure the sample is fully aerated. The aeration of the sample takes place at the beginning of the test.

The embedded computer 21 turns on a sample flow control 27, which is a pump used to deliver the sample throughout the thermal oxidation stability tester 20. Simultaneous with the sample flow control 27 pumping the test sample throughout the system, sample pressure control 29 maintains a fixed pressure throughout the system. It is important to maintain pressure in the system to prevent boiling of the test sample when at elevated temperatures. In the present thermal oxidation stability tester 20, the sample is maintained at approximately 500 psi when undergoing the thermal oxidation stability test.

Also, the embedded computer 21 controls parameters affecting the intelligent heater tube 33. The test data is recorded to the intelligent heater tube 33 via intelligent heater tube writer 35 from the embedded computer 21. Critical test parameters are recorded on a memory device (as described subsequently) on an end of the intelligent heater tube 33 via the intelligent heater tube writer 35. The rating of the deposit formed on the intelligent heater tube 33 will be recorded on the memory device at a later time.

In performing the thermal oxidation stability test on a test sample, the intelligent heater tube 33 is heated by tube heater control 37. The tube heater control 37 causes current to flow through the intelligent heater tube 33, which causes the intelligent heater tube 33 to heat up to the temperature setpoint.

To prevent the hot intelligent heater tube 33 from heating other parts of the thermal oxidation stability tester 20, bus-bar coolant control 39 provides coolant to upper and lower bus-bars holding each end of the intelligent heater tube 33. This results in the center section of the intelligent heater tube 33 reaching the prescribed temperature while the ends of the intelligent heater tube 33 are maintained at a lower temperature. This is accomplished by flowing coolant via the bus-bar coolant control 39 across the ends of the intelligent heater tube 33.

The test parameters, such as the dimension of the heater tube, pressure of the test sample or flow rate are fixed by ASTM D3241. However, the control of the equipment meeting these parameters are the focus of this invention.

Figure 2:
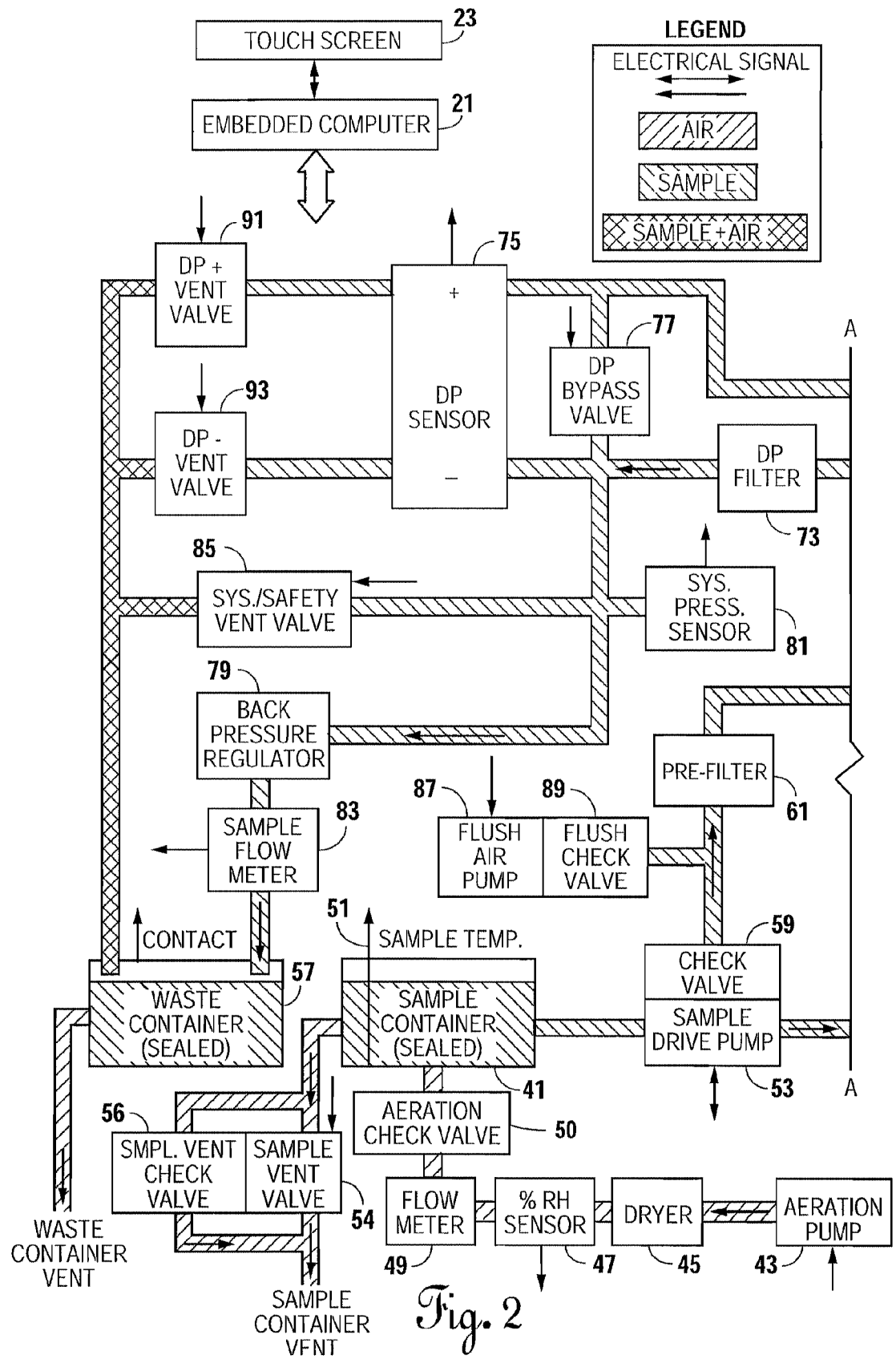
FIGS. 2 and 2A are a more detailed block diagram showing a thermal oxidation test apparatus used to perform the ASTM D3241 Standard.
Figure 2A:
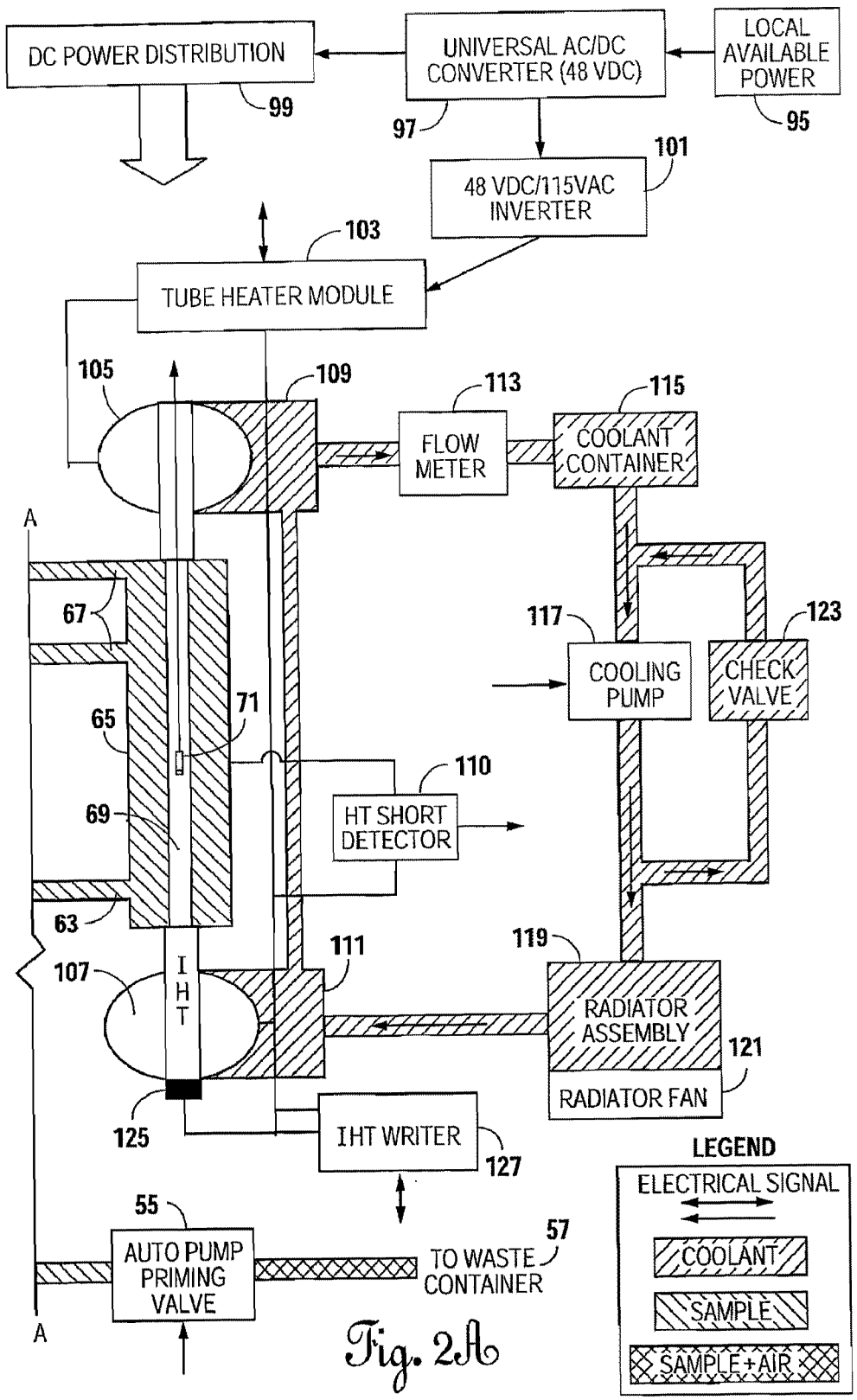

Referring now to FIGS. 2 and 2A in combination, a schematic flow diagram is shown connecting the mechanical and electrical functions. The embedded computer 21 and the touch screen 23 provide electrical signals as indicated by the arrows. A test sample is contained in the sample container 41. To make sure the sample in the sample container 41 is fully aerated, an aeration pump 43 is turned ON. The aeration pump 43 pumps air through a dryer 45 where the air is dehumidified. From the dryer 45, a percent relative humidify sensor 47 determines the humidity level of the pumped air and provides that information to the embedded computer 21. Assuming the percent humidity of the pumped air is sufficiently low, the test procedure will continue pumping air through the flow meter 49 and aeration check valve 50 into the sample container 41. During aeration, flow meter 49 should record approximately 1.5 liters of air per minute. Since the flow meter 49 runs for approximately six minutes, the aeration pump 43 will sparge approximately nine liters of air into the test sample. This is sufficient time to saturate the test sample with dry air.

Within the sample container 41, a sample temperature measurement 51 is taken and provided to the embedded computer 21. The sample temperature measurement 51 is to ensure that the test sample is between 15°-32° C. If the test sample is outside of this temperature range, results can be impacted. Therefore, if the test sample is outside this temperature range, the embedded computer 21 would not let the test start.

Once the test sample has been aerated and if all the other parameters are within tolerance, then the sample drive pump 53 will turn ON. The sample drive pump 53 is a single piston reciprocating pump, also known as a metering pump. With every stroke of the piston, a fixed volume of the sample is delivered. The speed of the sample drive pump 53 is controlled so that it pumps 3 mL/min of the test sample. The sample drive pump 53 is configured for fast refill which minimizes the need for manual pump priming. Pulsations associated with pumps of this design are minimized with the use of a pulse dampener and a coil tubing on the outlet side as will be subsequently described.

To get air out of the tubing between the sample container 41 and the sample drive pump 53 at the start of the test, an auto pump priming valve 55 is opened, a sample vent valve 54 is closed and the aeration pump 43 is turned ON by the embedded computer 21. The auto pump priming valve 55 opens and remains open while a combination of sample and air is discharged into waste container 57. At the same time the aeration pump 43 provides positive pressure in the sample container 41 to force test sample from the sample container 41 to the sample drive pump 53. The sample vent valve 54 closes to prevent venting of the air pressure to atmosphere and to maintain a pressure of 2 to 3 psi. A sample vent check valve 56 across the sample vent valve 54 opens at 5 psi to prevent the pressure in the sample container 41 from exceeding 5 psi. Once the sample drive pump 53 starts pumping the test sample, auto pump priming valve 55 will close and the sample vent valve 54 will open. Thereafter, the sample drive pump 53 will pump the test sample through check valve 59 to the prefilter 61. The check valve 59 prevents fluid from flowing backwards through the sample drive pump 53. The check valve 59 operates at a pressure of approximately 5 psi. The check valve 59 prevents siphoning when the sample drive pump 53 is not pumping. Also, check valve 59 prevents fluid from being pushed backwards into the sample drive pump 53.

The prefilter 61 removes solid particles in the test sample that could affect the test. The prefilter 61 is a very fine filter, normally in the order of 0.45 micron in size. The purpose of the prefilter 61 is to make sure particles do not get into the test filter as will be described. The prefilter 61 is replaced before every test.

From the prefilter 61, the test sample flows through an inlet 63 into the cylindrical heater tube test section 65. Outlet 67, while illustrated as two separate outlets, is actually a single outlet at the upper end of the cylindrical heater tube test section 65. Extending through the cylindrical heater tube test section 65 is the intelligent heater tube 69, which is sealed at each end with ceramic bushings and o-rings (not shown). While the test sample flows through the cylindrical heater tube test section 65 via inlet 63 and outlet 67 and around the intelligent heater tube 69, the housing of the cylindrical heater tube test section 65 is electrically isolated from the intelligent heater tube 69. Only the test sample comes in contact with the center section of the intelligent heater tuber 69. Inside of the intelligent heater tube 69 is a thermocouple 71 that sends a signal back to the embedded computer 21 as to the temperature of the center section of the intelligent heater tube 69.

Test sample flowing from the cylindrical heater tube test section 65 flows through a differential pressure filter 73, commonly called the "test filter". The intelligent heater tube 69 heats up the test sample inside of the cylindrical heater tube test section 65 to the test parameter set point. Heating of the test sample may result in degradation of the test sample, or cause solid particles to form. The solid particles may deposit on the center section of the intelligent heater tube 69, and/or may collect in the differential pressure filter 73. The pressure drop across the differential pressure filter 73 is measured by differential pressure sensor 75. Pressure across the differential pressure filter 73 is continuously monitored by the embedded computer 21 through the differential pressure sensor 75. When the pressure across the differential pressure filter 73 exceeds a predefined pressure difference of approximately 250 mm to 280 mm of mercury, the differential pressure bypass valve 77 opens to relieve the pressure. By test definition, exceeding a differential pressure of 25 mm Hg results in failure of the test sample.

For this test to be performed, the test sample must remain as a liquid. At testing temperatures of 250° C. to 350° C., many hydrocarbon fuels will transition to the vapor phase at ambient pressures. To keep the test sample in the liquid phase, the back pressure regulator 79 maintains approximately 500 psi pressure in the system. This system pressure is monitored by the system pressure sensor 81, which reports information to the embedded computer 21. During a test, normal flow of a test sample is through differential pressure filter 73 and through the back pressure regulator 79. From the back pressure regulator 79, the test sample flows through sample flow meter 83 to waste container 57. The sample flow meter 83 accurately measures the flow rate of the test sample during the test. The sample flow meter 83 provides sample flow rate information to the embedded computer 21.

A system/safety vent valve 85 is connected into the system and controlled via the embedded computer 21. The system/safety vent valve 85 acts to relieve excess system pressure in the case of power loss, improperly functioning system components or other system failures. In the event of this occurrence, the system pressure sensor 81 sends a signal to the embedded computer 21, triggering the system/safety vent valve 85 to open and relieve excess pressure. Also, at the completion of a test, the system/safety vent valve 85 opens to vent pressure from the system. The system/safety vent valve 85 is normally set to the open position requiring a program command from the embedded computer 21 to close the system/safety vent valve 85. Therefore, if power is lost, the system/safety vent valve 85 automatically opens.

At the end of the test, after the system/safety vent valve 85 is opened and system pressure is relieved, the flush air pump 87 turns ON and flushes air through flush check valve 89 to remove the test sample from the system. The flush air pump 87 pushes most of the test sample out of the system via the system/safety vent valve 85 into the waste container 57.

The system may not operate properly if there are air pockets or air bubbles in the system. During a test, it is important to maintain an air-free system. Therefore, at the beginning of each test, the solenoid operated differential pressure plus vent valve 91 and the differential pressure minus vent valve 93 are opened, flushed with test sample, and vented to remove any air pockets that may be present. During the beginning of each test, the position of the differential pressure vent valves 91 and 93 ensure there is no air in the differential pressure lines.

If the waste container 57 is properly installed in position, a signal will be fed back to the embedded computer 21 indicating the waste container 57 is correctly connected. This also applies for the sample container 41 which sends a signal to the embedded computer 21 when it is properly connected. The system will not operate unless both the waste container 57 and the sample container 41 are properly positioned.

The center portion of the intelligent heater tube 69 is heated to the test parameter set point by flowing current through the intelligent heater tube 69. Instrument power supplied for current generation and all other instrument controls is provided through local available power 95. Depending on local power availability, local available power 95 may vary drastically. In some areas it is 50 cycles/sec. and in other areas it is 60 cycles/sec. The voltage range may vary from a high of 240 Volts down to 80 Volts or less. A universal AC/DC converter 97 takes the local available power 95 and converts it to 48 Volts DC. With the universal AC/DC converter 97, a good, reliable, constant 48 Volts DC is generated. The 48 Volts DC from the universal AC/DC converter 97 is distributed throughout the system to components that need power through the DC power distribution 99. If some of the components need a voltage level other than 48 Volts DC, the DC power distribution 99 will change the 48 Volts DC to the required voltage level.

To heat the intelligent heater tube 69, the 48 Volts from the universal AC/DC converter 97 is converted to 115 Volts AC through 48 Volt DC/115 Volts AC inverter 101. While taking any local available power 95, running it through a universal AC/DC converter 97 and then changing the power back to 115 Volts AC through a 48 Volts DC/115 Volts AC inverter 101, a stable power supply is created. From the 48 Volts DC/115 Volts AC inverter 101, power is supplied to the heater tube module 103. The heater tube module 103 then supplies current that flows through the intelligent heater tube 69 via upper clamp 105 and lower clamp 107. The heater tube module 103 is controlled by the embedded computer 21 so that during a normal test, the thermocouple 71 inside of the intelligent heater tube 69 will indicate when the intelligent heater tube 69 has reached the desired temperature.

While the center section of the intelligent heater tube 69 heats to desired test set point, the ends of the intelligent heater tube 69 will be maintained near room temperature. To maintain the ends of the intelligent heater tube 69 near room temperature, a coolant flows through an upper bus-bar 109 and lower bus-bar 111. The coolant inside the upper bus-bar 109 and lower bus-bar 111 cools the upper clamp 105 and lower clamp 107 which are attached to the ends of the intelligent heater tube 69. The preferred cooling solution is a mixture of approximately 50% water and 50% antifreeze (ethylene glycol). As the coolant flows to the coolant container 115, the flow is measured by flow meter 113. To circulate the coolant, a cooling pump 117 pumps the coolant solution into a radiator assembly 119. Inside of the radiator assembly 119, the coolant is maintained at room temperature. The radiator fan 121 helps remove heat from the coolant by drawing air through the radiator assembly 119. From the radiator assembly 119, the coolant flows into the lower bus-bar 111 then through upper bus-bar 109 prior to returning via the flow meter 113.

The flow meter 113 is adjustable so that it can ensure a flow of approximately 10 gal./hr. The check valve 123 helps ensure the cooling system will not be over pressurized. Check valve 123 will open at around 7 psi, but normally 3-4 psi will be developed when running the coolant through the entire system.

To determine if the intelligent heater tube 69 is shorted out to the housing (not shown in FIGS. 2 and 2A), a heater tube short detector 110 monitors for a short condition. If a short is detected, the embedded computer 21 is notified and the test is stopped.

On one end of the intelligent heater tube 69 there is a memory device 125 to which information concerning the test can be recorded by IHT writer 127. While a test is being run on a test sample, the IHT writer 127 will record information into the memory device 125. At the end of the test, all electronic information will be recorded onto the memory device 125 of the intelligent heater tube 69, except for the manual tube deposit rating. To record this information, the intelligent heater tube 69 will have to be moved to another location to record the deposit rating as determined (a) visually or (b) through a Video Tube Deposit Rater. At that time, a second IHT writer will write onto the memory device 125. The Video Tube Deposit Rater may be built into the system or may be a standalone unit.

The intelligent heater tube 69 is approximately 6¾" long. The ends are approximately 3/16" in diameter, but the center portion that is heated is approximately ⅛" in diameter. Due to very low electrical resistance of aluminum, approximately 200 to 250 amps of current flows through the intelligent heater tube 69. Both the voltage across and the current through the intelligent heater tube 69 are monitored by the embedded computer 21. Also, the temperature of the center section of the intelligent heater tube 69 is monitored by the thermocouple 71, which is also connected to the embedded computer 21. The objective is to have the center section of the intelligent heater tube 69 at the required temperature. To generate that type of stable temperature, a stable source of power is provided through the universal AC/DC converter 97 and then the 48 VDC/115 VAC inverter 101. By using such a stable source of power, the temperature on the center section of the heater tube 69 can be controlled within a couple of degrees of the required temperature.

Figure 3:
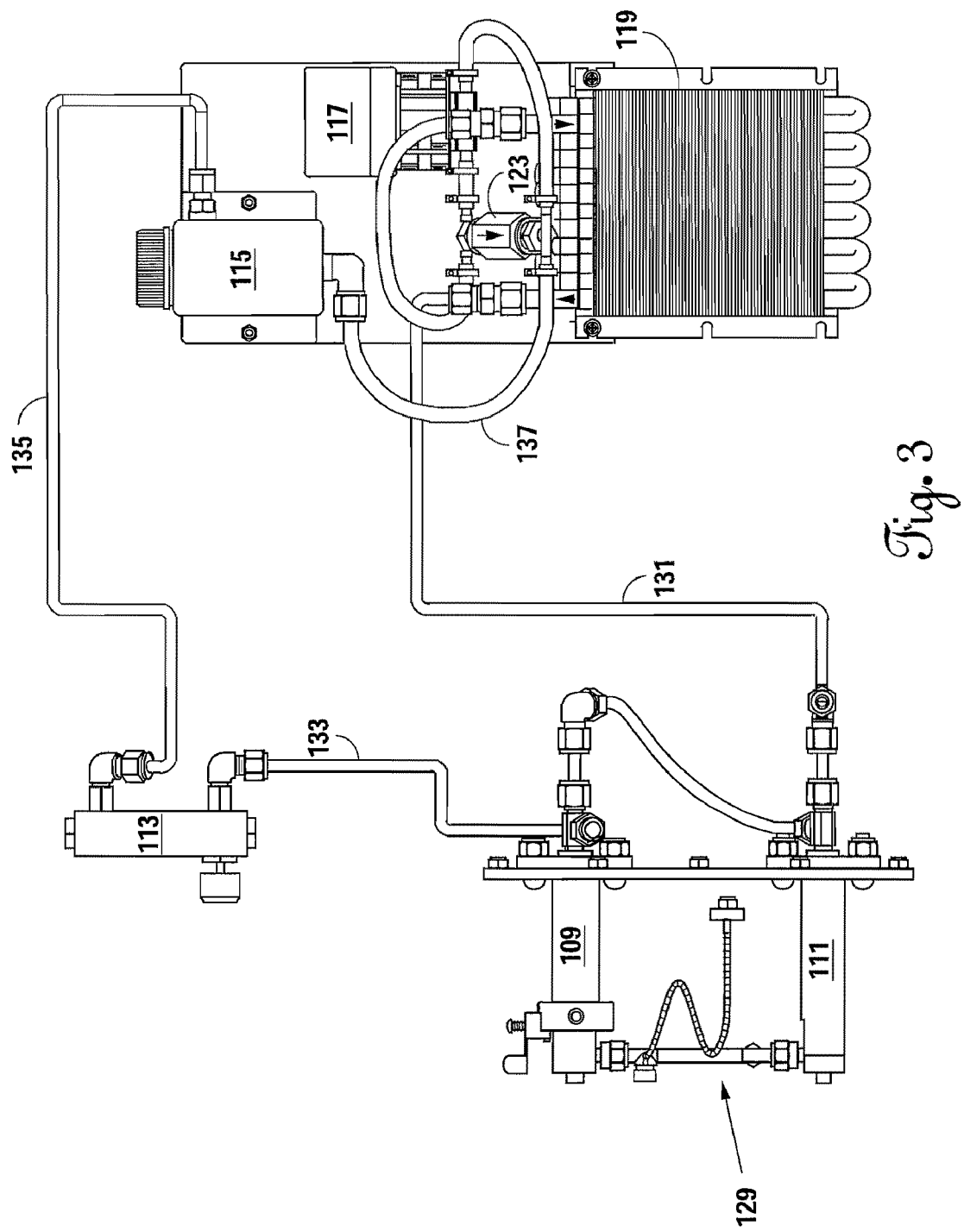
FIG. 3 is a pictorial diagram of the coolant flow for FIGS. 2 and 2A.

Referring now to FIG. 3 of the drawings, a pictorial representation of the coolant flow during a test is illustrated. Like numbers will be used to designate similar components as previously described. A pictorial illustration of the heater tube test section 129 is illustrated on the lower left portion of FIG. 3. Coolant from the radiator assembly 119 is provided to the lower bus-bar 111 and upper bus-bar 109 via conduit 131. From the upper bus-bar 109, the coolant flows via conduit 133 to flow meter 113. From flow meter 113, the coolant flows through conduit 135 to the coolant container 115. The cooling pump 117 receives the coolant through conduit 137 from the coolant container 115 and pumps the coolant into radiator assembly 119. If the pressure from the cooling pump 117 is too high, check valve 123 will allow some of the coolant to recirculate around the cooling pump 117. FIG. 3 is intended to be a pictorial representation illustrating how the coolant flows during a test.

Figure 4:
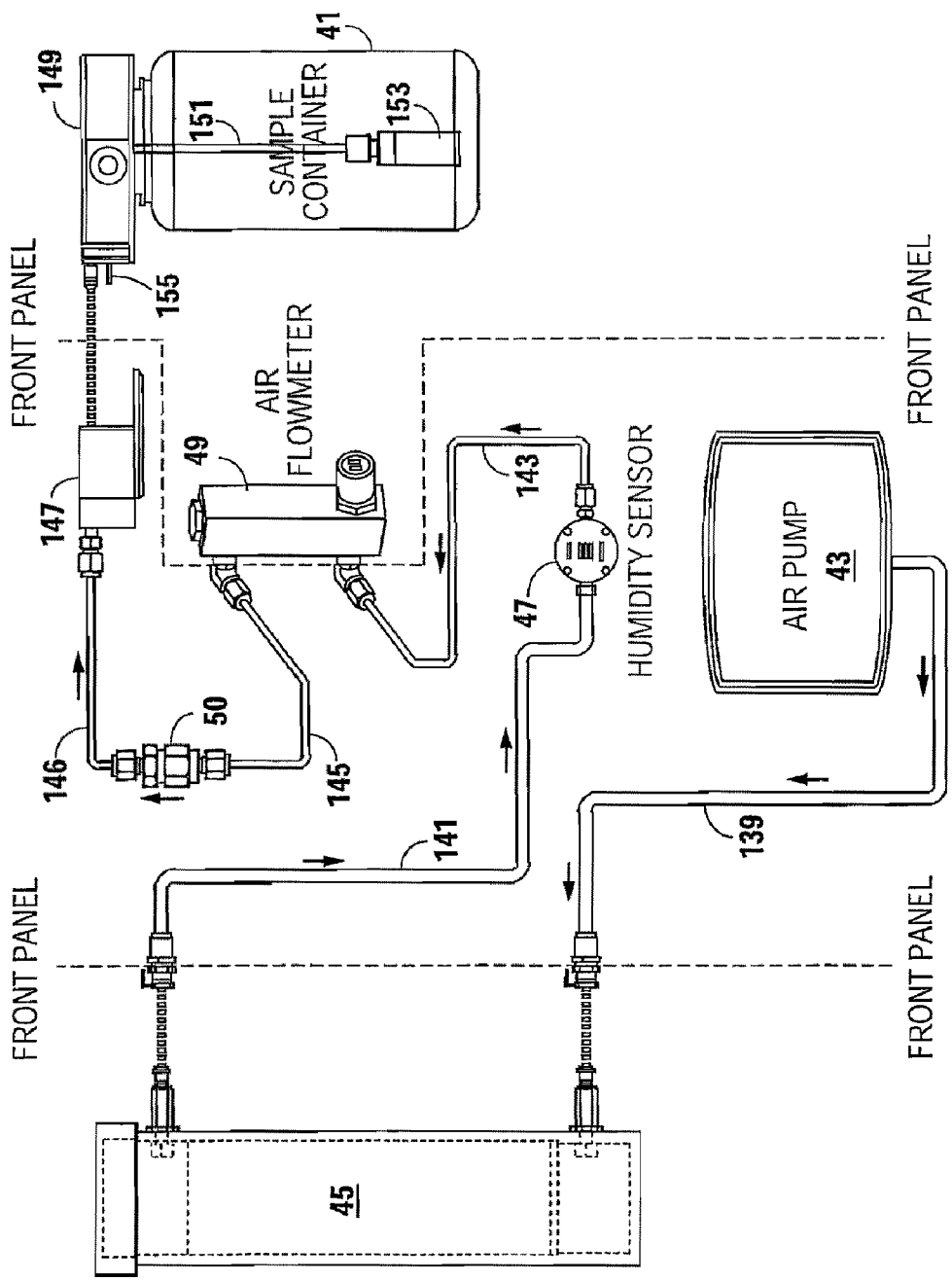
FIG. 4 is a pictorial diagram of the airflow in FIGS. 2 and 2A

Likewise, FIG. 4 is a pictorial representation of the aeration system for the test sample. Similar numbers will be used to designate like components as previously described. An aeration pump 43 pumps air through conduit 139 to a dryer 45. The dryer 45 removes moisture from the air to prevent the moisture from contaminating the test sample during aeration. From the dryer 45, the dried air will flow through conduit 141 to humidity sensor 47. If the percent relative humidity of the dried air blowing through conduit 141 exceeds a predetermined amount of 20% relative humidity, the system will shut down. While different types of dryers 45 can be used, it was found that Dry-Rite silica gel desiccant is an effective material for producing the desired relative humidity.

From the percent humidity sensor 47, the dried air flows through conduit 143 to flow meter 49, which measures the air flow through conduit 143 and air supply conduit 145. From air supply conduit 145, the dried air flows through aeration check valve 50 and conduit 146 to sample container arm mounting clamp 147 and sample container arm 149 to aeration conduit 151 located inside of sample container 41. In the bottom of sample container 141, a glass frit 153 connects to aeration conduit 151 to cause the dried air to sparge through the test sample in sample container 41. When the sample container 41 is in place and the sample container arm 149 is connected to the sample container arm mounting clamp 147, contact 155 sends a signal to the embedded computer 21 (see FIG. 2) indicating the sample container 41 is properly installed.

Figure 5:
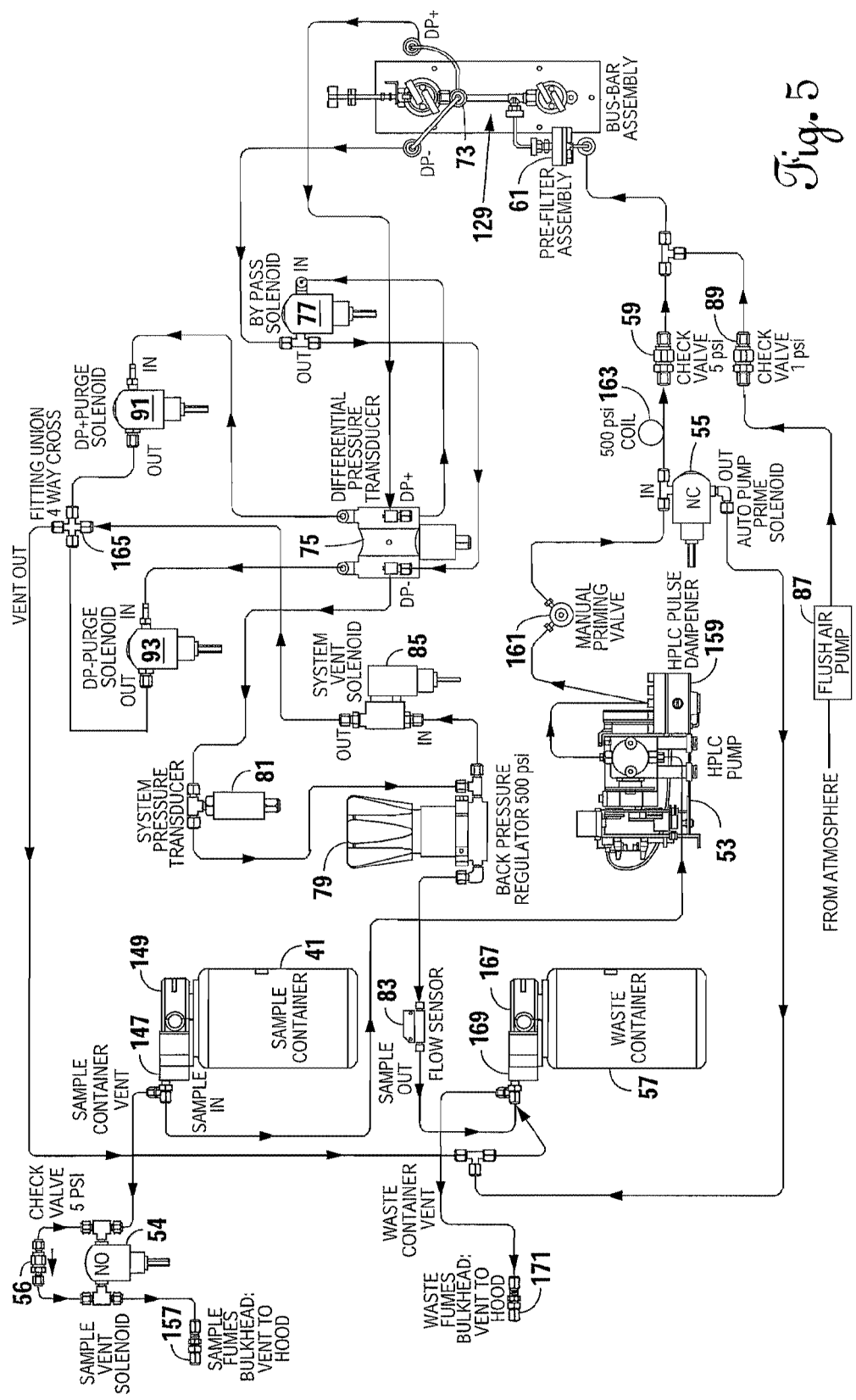
FIG. 5 is a pictorial diagram showing flow of the test sample in FIGS. 2 and 2A.

Referring now to FIG. 5, a pictorial illustration of the flow of the test sample in connection with FIGS. 2 and 2A is shown in a schematic flow diagram. The test sample is contained in sample container 41, which is connected via sample container arm 149 to the sample container arm mounting clamp 147. Vapors given off by the test sample are discharged through a vent 157, normally through a vent hood to atmosphere. Simultaneously, the sample drive pump 53 draws some of the test sample out of the sample container 41. The sample drive pump 53 is a single piston reciprocating pump connected to a pulse dampener 159. While the pulse dampener 159 may be configured a number of ways, the pulse dampener 159 in the preferred configuration has a diaphragm with a semi-compressible fluid on one side of the diaphragm. This fluid is more compressible than the test sample thereby reducing pressure changes on the test sample flow discharged from the sample drive pump 53. The sample drive pump 53 is connected to auto pump priming valve 55. During start-up, the closed auto pump priming valve 55 opens until all of the air contained in the pump and the lines are discharged into the waste container 57. In case it is needed, a manual priming valve 161 is also provided. Additionally, the aeration pump 43 (see FIG. 2) is turned ON to provide a slight pressure in the sample container 41 of about 2 to 3 psi. The sample vent valve 54 closes to prevent this pressure from escaping to atmosphere. This pressure will help push the fluid sample from the sample container 41 to the inlet of the sample drive pump 53. The 5 psi check valve 56 prevents the pressure in the sample container exceeding 5 psi. During the test, coil 163 also provides further dampening in addition to the pulse dampener 159. Check valve 59 ensures there is no back flow of the sample fuel to the sample drive pump 53. However, at the end of a test, flush check valve 89 receives air from flush air pump 87 to flush the test sample out of the system.

During normal operation of a test, the sample fuel will flow through check valve 59 and through a prefilter 61 removing most solid particles. Following the prefilter 61, the test sample flows into the heater tube test section 129 and then through the differential pressure filter 73. Each side of the differential pressure filter 73 connects to the differential pressure sensor 75. Also connected to the differential pressure filter 73 is the back pressure regulator 79. The pressure on the system is continuously monitored through the system pressure transducer 81. If for any reason pressure on the system needs to be released, system/safety vent valve 85 is energized and the pressurized test sample is vented through the four-way cross connection 165 to the waste container 57.

At the beginning of the test, to ensure there is no air contained in the system, the differential pressure plus vent valve 91 and the differential pressure minus vent valve 93 are opened to vent any pressurized fluid through the four-way cross connection 165 to the waste container 57.

In case the differential pressure filter 73 clogs so that the differential pressure exceeds a predetermined value, differential pressure bypass valve 77 will open to relieve the pressure.

To determine the exact flow rate of the test sample through the system, the sample flow meter 83 measures the flow rate of test sample from the back pressure regulator 79 before being discharged through the waste container arm 167 and the waste container clamp 169 into the waste container 57. The waste container 57 is vented all the time through vent 171.

Figure 6A:
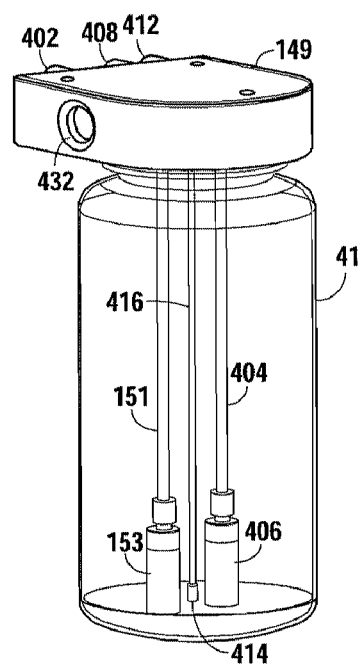
FIG. 6A is a perspective view of the sample container.
Figure 6B:
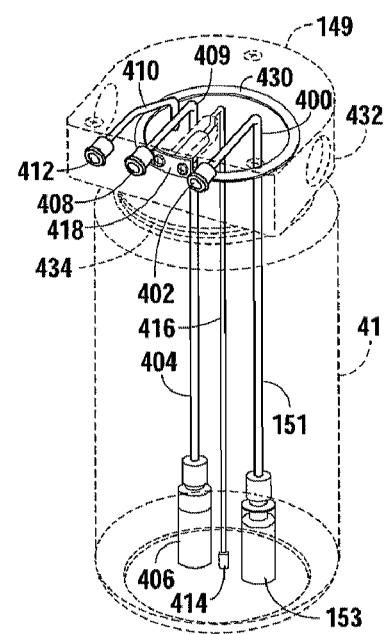
FIG. 6B is a perspective view of the internal components of the sample container.

Referring to FIGS. 6A and 6B, a sample container 41 and the sample container arm 149 are illustrated in further detail. A glass frit 153 is located near the bottom of the sample container 41. A glass frit 153 connects through aeration conduit 151, elbow 400 in sample container arm 149 to sealing connector 402. Sealing connector 402 will mate with a receiving connector in the sample container arm mounting clamp 147 (see FIG. 4). As air is blown through the glass frit 153 by the air pump 43, the air will form small bubbles and sparge through the test sample. Small bubbles are preferred as they have more surface area and more readily dissolve in the test sample. More detail will be given on the glass frit 153 herein below.

Also extending to the bottom of the sample container 41 is a suction line 404 with a coarse filter 406 on the end thereon. While the coarse filter 406 can be of any particular type, it could be similar glass frit 153. The coarse filter 406 is designed to remove larger solid particles that may be in the test sample. The suction line 404 connects through elbow 409 in sample container arm 149 to the suction connector 408. The suction connector 408 connects to a mating connector (not shown) in the sample container arm mounting clamp 147 (see FIG. 4).

Also connecting through sample container arm 149 to the top of sample container 41 is vent line 410. The lower end of vent line 410 terminates below sample container arm 149 but at the top of sample container 41. The opposite end of vent line 410 connects to vent connector 412 which further connects to vent 157 (see FIG. 2 and FIG. 5).

Located near the bottom of sample container 41 is a thermocouple 414 for measuring the temperature of the test sample. The thermocouple 414 sends a signal through thermocouple connection 416 to thermocouple plate 418 in sample container arm 149. In the sample container arm mounting clamp 147, an electrical connection with the thermocouple plate 418 will be made and the signal from the thermocouple 414 will be sent to the embedded computer 21 shown in FIG. 2. Also, if a signal is being received from the thermocouple 414 through thermocouple plate 418, that indicates the sample container 41 is in position and the test can begin.

Referring to FIGS. 7A and 7B in combination, the waste container 57 and waste container arm 167 are shown in more detail. The waste container arm 167 has a vent line 470 connecting to vent connector 472 the same as was shown in connection with FIGS. 6A and 6B of the sample container arm 149. However, the vent line 470 and vent connector 472 in waste container arm 167 connects to the vent 171 for the waste container 57 (see FIG. 5).

During the operation of a test, test sample flow line 420 receives the spent sample from the test through sample connection 422. Sample connection 422 connects with a mating connector (not shown) in the waste container clamp 169 to receive the spent sample after test from the sample flow meter 83 (see FIG. 2).

Either when starting up a test or shutting down a test, venting or purging of the system is necessary through vent/purge line 424 and vent/purge connector 426. The vent/purge connector 426 has a mating connector (not shown) in waste container clamp 169. The vent/purge line 424 and vent/purge connector 426 receive any fluid or air discharged from system vent valve 85, differential pressure plus vent valve 91 and differential pressure minus vent valve 93. Also any air or fuel from the auto pump priming valve 55 will be received through the vent/purge line 424. The vent line 470, test sample flow line 420 and vent/purge line 424 all terminate just below the waste container arm 167 in the top of waste container 57.

A shorting plate 428 is contained on the face of the waste container arm 167. Two electrical connections extend through the waste container clamp 169 (see FIG. 5) so that if the two connections are shorted by the shorting plate 428, the embedded computer 21 will know the waste container 57 is in position.

Sealing the top of the sample container 41 and the waste container 57 is a flexible washer 430. It is important that the material of the flexible washer 430 is compatible with fuels or similar petroleum-based products.

On the side of both the sample container arm 149 and the waster container arm 167 are indentations 432 that can be used for gripping the container arms thereto for installing or removing the respective clamps 147 or 169.

With the exception of providing a connection for the thermocouple 414 there through, the sample container arm 149 and the waste container arm 167 are essentially identical. However, the spacing on the connectors are different so that they cannot be mistakenly interchanged. While the sample container arm 149 and waste container arm 167 can be molded as an integral piece, in this preferred embodiment a fuel resistant epoxy is used to seal both the sample container arm 149 and the waste container arm 167 into a solid piece.

The sample container arm 149 threadably connects in the bottom thereof to threads 434 in the top of the sample container 41. Likewise, waste container arm 167 threadably connects to waster container 57 through threads 436. When either the sample container 41 or the waste container 57 is threadably connected in the proper position, flexible washer 430 will seal against leakage. The sample container 41 and the waste container 57 are made from a fuel resistant plastic such as plyolefin or glass.

Figure 8A:
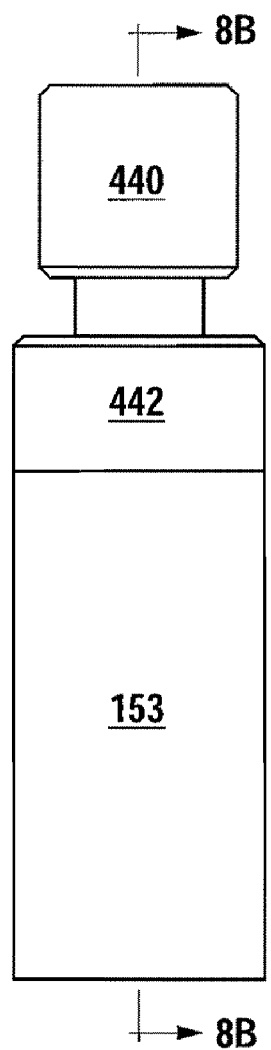
FIG. 8A is an elevated view of the aeration frit.
Figure 8B:
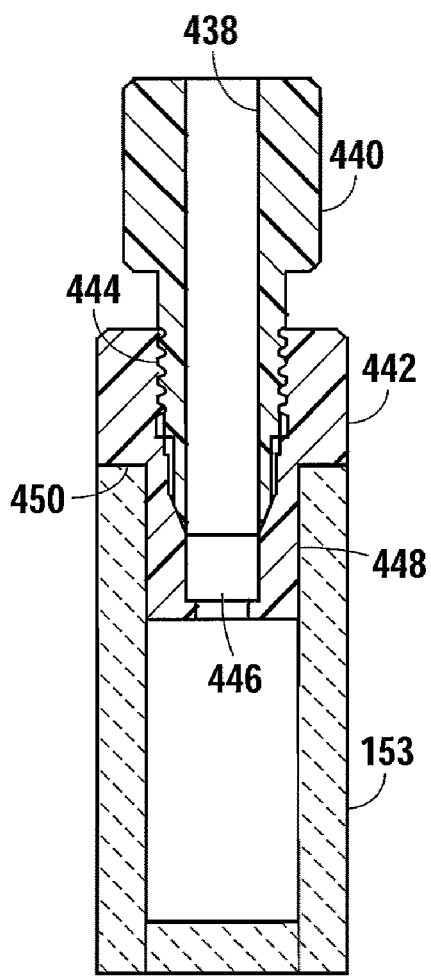
FIG. 8B is a cross sectional view of FIG. 8A along section lines 8B-8B.

Referring now to FIGS. 8A and 8B, the glass frit 153 is shown in more detail. The aeration conduit 151 (see FIGS. 6A and 6B) is received in upper opening 438 of fitting 440. Fitting 440 is a standard fitting for ⅛" diameter tubing. The aeration conduit 151 is ⅛" in diameter. Between the fitting 440 and the glass frit 153 is a frit cap 442. The frit cap 442 is machined to receive the lower thread 444 to threadably connect with fitting 440. On the upper part is inside passage 446 of frit cap 442. The lower outside cylindrical portion 448 of the frit cap 442 is machined to fit just inside of glass frit 153 and has a shoulder 450 to abut the top of the glass frit 153. The frit cap 442 is made from a fuel resistant material so it will not corrode.

While many different types of glass frit 153 could be used, in this preferred embodiment, Applicant used a coarse frit made out of glass that has a 12 mm outside diameter, 6 mm inside diameter and 25 mm in length. To connect the glass frit 153 to the frit cap 442, a fuel-resistant adhesive is used. The flexible washer 430 (see FIG. 6B) may be made of a Viton closed cell rubber gasket.

What we claim is:

1. An apparatus for testing thermal oxidation stability of a test sample such as a hydrocarbon fuel comprising:
a source of electric power;
a heater tube connected to said source of electric power for flowing current to heat a center section of said heater tube to a predetermined temperature;
a coolant flow circuit supplying coolant to each end of said heater tube to keep each end thereof near room temperature;
an aeration circuit with an aeration pump for pumping air to aerate said test sample in a sample container;
a test sample flow circuit for flowing said test sample around said center section to heat said test sample to said predetermined temperature, said test sample flow circuit including:
a sample drive pump pumping said test sample from said sample container around said center section of said heater tube;
a differential pressure filter in said test sample flow circuit after said heater tube to filter out any solids that may have formed in said test sample when heated to said predetermined temperature due to oxidation of said test sample;
a differential pressure sensor for measuring differential pressure across said differential pressure filter;
a back pressure regulator for maintaining said test sample being pumped by said sample drive pump at a test pressure high enough to keep said test sample in a liquid phase when heated to said predetermined temperature;
a waste container for collecting said test sample after said test;
said sample container and said waste container being sealed to prevent spilling of said test sample, yet selectively providing venting to said sample container during said testing.

2. The apparatus for testing thermal oxidation stability of said test sample as recited in claim 1 wherein said aeration circuit includes an aerator in said sample container to sparge air from an aeration pump through said test sample.

3. The apparatus for testing thermal oxidation stability of said test sample as recited in claim 2 wherein said aerator is a coarse glass frit mounted near the bottom of said sample container on an end of an aeration conduit, said coarse glass frit causing small bubbles of air in said test sample.

4. The apparatus for testing thermal oxidation stability of said test sample as recited in claim 3 wherein said coarse glass frit has a fitting between said coarse glass frit and said aeration conduit, a lower end of said fitting being bonded to an upper end of said coarse glass frit.

5. The apparatus for testing thermal oxidation stability of said test sample as recited in claim 2 wherein said sample container has (a) an aeration conduit connected to said aeration pump and extending into said sample container, (b) a suction line from said sample container to said sample drive pump, and (c) a vent line from said sample container to atmosphere.

6. The apparatus for testing thermal oxidation stability of said test sample as recited in claim 5 wherein said vent line may be selectively closed by a sample vent valve.

7. The apparatus for testing thermal oxidation stability of said test sample as recited in claim 6 wherein said sample container has a thermocouple therein for measuring temperature of said test sample to determine if said test sample is of a temperature suitable for said testing.

8. The apparatus for testing thermal oxidation stability of said test sample as recited in claim 1 wherein said sample container connects to a sample container arm and said waste container connects to a waster container arm.

9. The apparatus for testing thermal oxidation stability of said test sample as recited in claim 8 wherein said sample container arm and said waste container arm are made of a solid construction.

10. The apparatus for testing thermal oxidation stability of said test sample as recited in claim 8 wherein said sample container arm and said waste container arm have electrical connections therein to indicate if in position for said testing.

11. The apparatus for testing thermal oxidation stability of said test sample as recited in claim 1 wherein said waste container (1) receives said test sample after said testing, (2)

receives a combination of said test sample and air during start up or a ending said testing and (3) vents to atmosphere to remove pressure there from.

12. A method of testing a test sample in liquid form for thermal oxidation stability comprising the following steps:
   aerating said test sample in a sample container with dry air to saturate said test sample with oxygen;
   heating a center section of a heater tube to a predetermined temperature by flowing current there through;
   cooling each end of said heater tube by flowing coolant from a coolant flow circuit to said each end;
   pumping said test sample at a low flow rate around said center section of said heater tube so that temperature of said test sample is raised to approximately said predetermined temperature;
   test filtering with a differential pressure filter said test sample to collect solids formed in said test sample when heated to said predetermined temperature;
   maintaining an elevated pressure on said test sample during said pumping step sufficient to keep said test sample from evaporating;
   discharging said test sample to a waste container;
   first venting said waste container to prevent other than atmospheric pressure therein;
   second venting of said sample container to atmosphere, and
   interrupting said second venting before said pumping step to cause a slightly higher than ambient pressure in sample container during priming for said pumping step.

13. The method of testing the test sample in liquid form for thermal oxidation stability as recited in claim 12 wherein said aeration step includes sparging air from a coarse glass frit in said sample container up through said test sample to saturate said test sample with air before said pumping step.

14. The method of testing the test sample in liquid form for thermal oxidation stability as recited in claim 13 wherein said coarse glass frit is bonded to a transition fitting with a fuel resistant adhesive, which transition fitting connects to the aeration conduit.

15. The method of testing the test sample in liquid form for thermal oxidation stability as recited in claim 13 includes an additional step of first monitoring temperature of said test sample in said sample container to keep said test sample near room temperature and second monitoring of said center section to ensure said predetermined temperature is maintained during said pumping step.

16. The method of testing the test sample in liquid form for thermal oxidation stability as recited in claim 15 wherein said discharging step includes said waste container (a) receiving said test sample after said testing, (b) receiving a combination of said test sample and air during priming or system venting, and (c) removing pressure there from.

17. The method of testing the test sample in liquid form for thermal oxidation stability as recited in claim 12 wherein said sample container (a) during said aeration step sparges air through said test sample, (b) provides a suction line to said test sample during said pumping step, (c) connects a thermocouple in said test sample to an embedded computer, and (d) using the thermocouple signal by said embedded computer to automatically check if the sample container is installed in place for said testing.

18. A sample container apparatus for use in a testing apparatus for determining thermal oxidation stability of a test sample, said sample container apparatus comprising:
   a sample container with an opening at the top thereof;
   a sample container arm closing said opening, said sample container arm being constructed to mate with a sample container clamp in said testing apparatus;
   an aerator conduit connecting from near the bottom of said sample container, through said sample container arm, to said testing apparatus to receive dry air there from to sparge said test sample;
   a suction line connecting from near said bottom of said sample container, through said sample container arm, to said testing apparatus to deliver said test sample thereto;
   a vent line connecting from near a top of said sample container through said sample container arm, to atmosphere via a vent hood; and
   a thermocouple near said bottom of said sample container to measure temperature of said test sample, a temperature signal from said thermocouple feeding through said sample container arm to said testing apparatus.

19. The sample container apparatus for use in the testing apparatus for determining thermal oxidation stability of the test sample as given in claim 18 wherein said vent line is selectively closed when starting a test to create a slightly higher than ambient pressure in said sample container to force said test sample through said suction line to said testing apparatus.

20. The sample container apparatus for use in the testing apparatus for determining thermal oxidation stability of the test sample as given in claim 19 wherein during said selective closing of said vent line, providing pressure relief if said slightly higher than ambient pressure exceeds a predetermined pressure limit.

21. The sample container apparatus for use in the testing apparatus for determining thermal oxidation stability of the test sample as given in claim 18 wherein said sample container seals to said sample container arm.

22. The sample container apparatus for use in the testing apparatus for determining thermal oxidation stability of the test sample as given in claim 21 wherein said suction line has a filter on a distal end thereof to remove large particles from said test sample.

23. The sample container apparatus for use in the testing apparatus for determining thermal oxidation stability of the test sample as given in claim 18 wherein a frit is located on a distal end of said aeration conduit to sparge said test sample with said dry air.

24. The sample container apparatus for use in the testing apparatus for determining thermal oxidation stability of the test sample as given in claim 23 wherein said frit is made from glass.

25. The sample container apparatus for use in the testing apparatus for determining thermal oxidation stability of the test sample as given in claim 24 further including a transition fitting between said glass frit and said aeration conduit.

26. The sample container apparatus for use in the testing apparatus for determining thermal oxidation stability of the test sample as given in claim 25 wherein said transition fitting is bonded to said glass frit with a fuel resistant sealant.

27. The sample container apparatus for use in the testing apparatus for determining thermal oxidation stability of the test sample as given in claim 18 wherein said sample container arm has a feedback plate for receiving said temperature signal and connecting to said testing apparatus when said sample container is in position for testing.

* * * * *